United States Patent
Edmundson et al.

(10) Patent No.: US 8,348,824 B2
(45) Date of Patent: Jan. 8, 2013

(54) TRANSPARENT CATHETERS FOR ENDOSCOPIC LOCALIZATION

(75) Inventors: Gregory K. Edmundson, Rough & Ready, CA (US); Jeffrey C. Mullins, Pleasanton, CA (US)

(73) Assignee: Cytyc Corporation, Marlborough, MA (US)

( * ) Notice: Subject to any disclaimer, the term of this patent is extended or adjusted under 35 U.S.C. 154(b) by 1347 days.

(21) Appl. No.: 11/947,849

(22) Filed: Nov. 30, 2007

(65) Prior Publication Data

US 2009/0143633 A1    Jun. 4, 2009

(51) Int. Cl.
*A61N 5/00* (2006.01)

(52) U.S. Cl. ............................................... 600/3; 604/21

(58) Field of Classification Search ................... 600/1–8, 600/585, 587, 591, 593; 604/19–21, 27, 604/28, 36, 93.01, 96.01, 103.01, 506–509, 604/514–517; 606/13–19, 33–46
See application file for complete search history.

(56) References Cited

U.S. PATENT DOCUMENTS

| | | | |
|---|---|---|---|
| 5,002,558 A | | 3/1991 | Klein et al. |
| 5,188,596 A | * | 2/1993 | Condon et al. ............. 604/103.1 |
| 5,314,443 A | | 5/1994 | Rudnick |
| 5,830,179 A | * | 11/1998 | Mikus et al. ................. 604/517 |
| 5,882,290 A | | 3/1999 | Kume |
| 6,261,219 B1 | * | 7/2001 | Meloul et al. ..................... 600/3 |
| 6,540,655 B1 | * | 4/2003 | Chin et al. ......................... 600/3 |
| 6,607,477 B1 | * | 8/2003 | Longton et al. ................... 600/3 |
| 6,796,976 B1 | | 9/2004 | Chin et al. |
| 6,942,648 B2 | | 9/2005 | Shaible et al. |

* cited by examiner

*Primary Examiner* — Charles A Marmor, II
*Assistant Examiner* — Carrie R Dorna

(57) ABSTRACT

Devices and methods are disclosed for the direct visualization and localization of a target area within a body lumen through the optically clear walls of a graduated catheter. An elongated catheter has proximal and distal ends, an anchor, graduated markings, and outer and inner surfaces defining a catheter wall. The anchor establishes a secure relationship between the catheter and an anatomical feature. The graduated markings are disposed along a length of the catheter. The outer surface of the catheter wall is configured for contacting a body lumen and the inner surface of the catheter wall defines a main lumen disposed along a length of the elongated catheter. The catheter wall is transparent along a length to provide visualization of the graduated markings via a visualization tool positioned in the main lumen. In one embodiment, a catheter may have a substantially circular cross-section and include an arc-shaped transparent window.

24 Claims, 4 Drawing Sheets

TRANSPARENT CATHETERS FOR ENDOSCOPIC LOCALIZATION

TECHNICAL FIELD

Devices and methods for the direct visualization and identification of an area of interest within a body lumen through the transparent walls of a graduated catheter.

BACKGROUND

Brachytherapy is the delivery of a course of radiation therapy to a body site by placing the radiation source into the body site. Usually, an implantable device (e.g., catheter, cannula, or applicator) is inserted into the body site and later a radiation source is inserted through the catheter and into the body site. Radiation therapy may be administered through one of several methods, or a combination of methods, such as interstitial or intercavity brachytherapy. Brachytherapy may also be administered using radioactive sources or electronic sources, such as x-ray sources, for example.

Conventional methods of determining the precise location that the radiation source(s) should be inserted into the catheter include inserting a calibrated marker wire into the catheter and using external imaging (e.g., radiographic, MRI, or ultrasound). From the resultant images, the precise position of the target tissue relative to the catheter and the inserted calibrated wire may then be determined. Once the position of the target tissue is known relative to the catheter and the calibrated wire, the location for positioning the radiation source within the catheter may then be calculated. The optimal dwell times for source treatment position are also determined using commercially available software. These activities are collectively called treatment planning.

Determining the precise location of the target tissue (i.e., the position of the radiation source(s)) is a critical step in the treatment planning process. Use of conventional methods using external imaging to determine target tissue location have several disadvantages including increased time and cost, as well as problems arising from miscalculation of offset distances and problems arising from slipping or movement of the catheter after the external imaging has been completed but before the treatment has been completed.

Therefore, it would be desirable to have devices and methods for precisely locating the position of the catheter relative to the target tissue (i.e., position of the radiation source(s)) to enhance treatment planning. Disclosed herein are graduated transparent catheters, and methods for using same, configured to provide direct visualization and identification of target tissues (i.e., position of the radiation source(s)).

SUMMARY

Disclosed herein are devices and methods for determining dwell positions of a treatment source. In particular, the devices include catheters which may be composed of transparent materials with graduated markings disposed along their length. Once a catheter is implanted into a body lumen, the exact position of an anatomical feature or target tissue may be determined using a remote visualization tool that is inserted through a lumen of the implanted catheter. The visualization tool is used to examine the relevant anatomy through the transparent wall of the catheter. By reading the graduated markings which are printed on, or embedded into, the transparent wall of the catheter, a determination may be made as to the exact distance a radiation source must be inserted into the catheter to reach the target tissue or anatomical feature. These distances may then be converted into offsets (the total distance that the radiation source needs to be extended). Determination of the offsets and dwell times is essential for the completion of the treatment planning process.

The graduated catheters and methods disclosed herein provide direct visualization of anatomical features of a body lumen from within the catheter. These graduated catheters and methods also provide direct visualization of graduated markings contained on or within the catheter. The ability to directly visualize the anatomical features of a body lumen and the graduated markings on the catheter provides a user with a direct measurement of the location of the anatomical feature for accurately determining the proper dwell position for a treatment source.

In one embodiment, an elongated catheter comprises proximal and distal ends, an anchor, graduated markings, and outer and inner surfaces defining a catheter wall. The anchor is disposed on the distal end of the elongated catheter and configured to establish a secure relationship between the elongated catheter and an anatomical feature. The graduated markings are disposed along a length of the catheter. The outer surface of the catheter wall is configured for contacting a body lumen and the inner surface of the catheter wall defines a main lumen disposed along a length of the elongated catheter. The catheter wall is transparent along a length of the elongated catheter to provide visualization of the graduated markings via a visualization tool positioned in the main lumen.

In another embodiment, a graduated catheter comprises outer and inner surfaces defining a catheter wall. The outer surface of the catheter wall is configured for contacting a body lumen and the inner surface of the catheter wall defines a main lumen disposed along a length of the elongated catheter. The catheter wall has a substantially circular cross-section and includes an approximately 60° arc-shaped transparent window for viewing graduated markings on the catheter in relation to the body lumen via a visualization tool positioned in the main lumen.

In yet another embodiment, a method for directly identifying an anatomical feature in a body lumen comprises: inserting a graduated catheter into a body lumen, the graduated catheter comprising outer and inner surfaces defining a catheter wall, wherein the outer surface of the catheter wall is configured for contacting the body lumen and wherein the inner surface of the catheter wall defines a main lumen disposed along a length of the elongated catheter, the catheter wall begin transparent along a length to provide a direct visualization of the body lumen via the main lumen; inserting a visualization tool into the main lumen of the graduated catheter to directly view an anatomical feature in the body lumen; viewing the anatomical feature through the transparent catheter wall using the visualization tool; and identifying the location of the anatomical feature in the body lumen relative to graduated markings on the graduated catheter.

DETAILED DESCRIPTION

Figure 1:
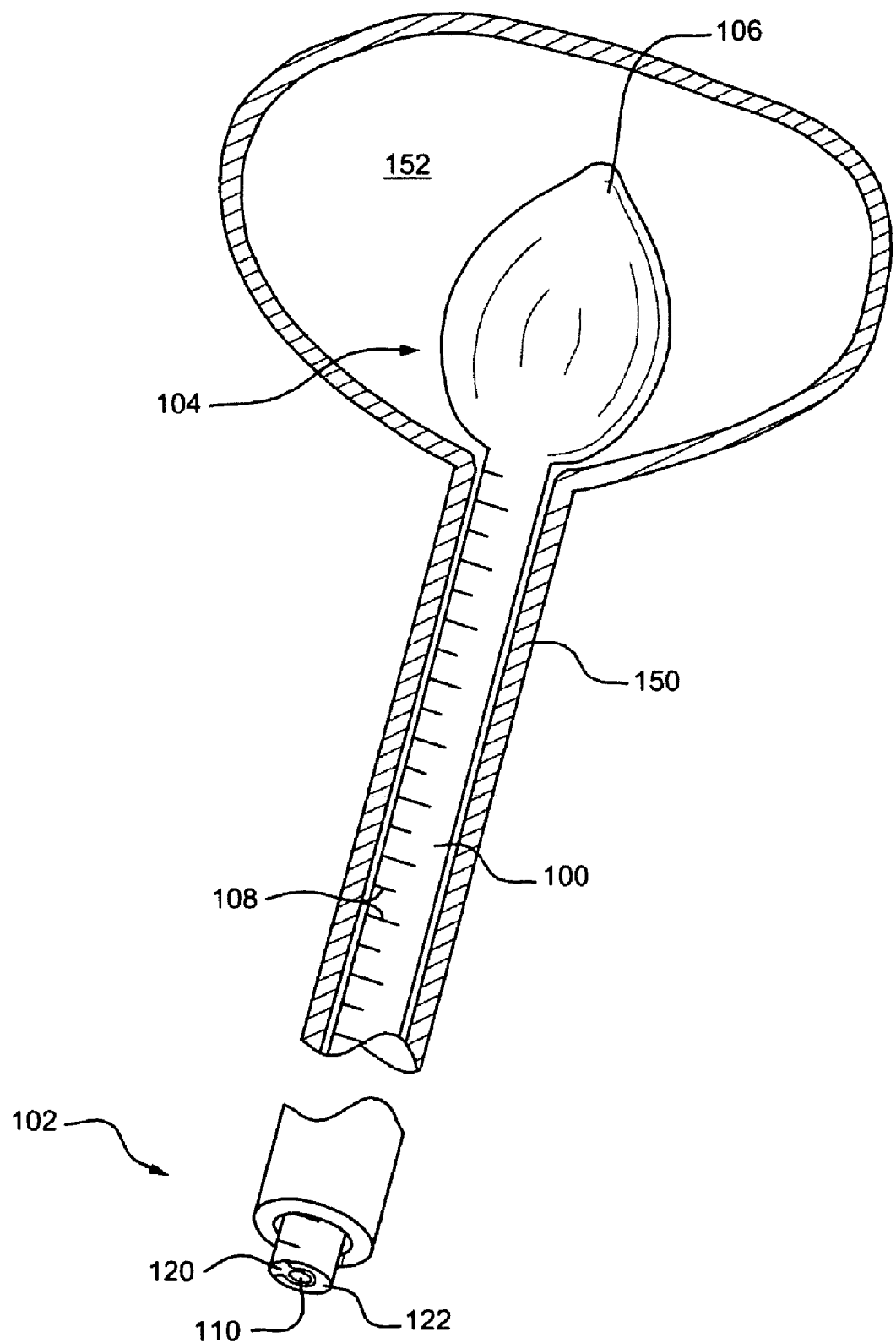
FIG. 1 illustrates a perspective view of an exemplary graduated urethral catheter.

Disclosed herein are devices and methods for precisely locating areas of interest within a body lumen for further medical treatment.

The devices disclosed herein comprise a cannula or catheter which may be inserted into a lumen in a patient's body through an orifice or other body opening and anchored within the patient's body. Once the catheter is securely anchored in the patient's body, a remote viewing device is introduced into the lumen of the catheter and advanced until the user can visualize the anatomical feature or area of interest through the transparent wall of the catheter while referencing the graduated markings on the catheter. Once location of the area of interest has been accurately identified relative to the markings, the user may insert another instrument into the catheter for treatment of, or manipulation of, the area of interest.

In one embodiment, the catheter may be designed to facilitate the localization of a urethral stricture for the delivery of therapeutic rays. Urethral stricture is a common complication of urological procedures, particularly following urethral intervention by a urologist (Baskin et al., 1993, J. Urology 150:642-647; Stormont et al., 1993, J. Urology 150:1725-1728). Formation of a urethral structure is thought to involve disruption of the urothelium, followed by hypertrophy of urothelial or other tissues, resulting in stenosis. A urethral stricture may also be formed by hypertrophy of a tissue located in close proximity to the urothelium, such as prostate tissue or corpus spongiosum penis tissue in male humans or muscle tissue or spongiose erectile tissue in female humans.

Non-limiting examples of urological interventions known to be associated with urethral stricture include transurethral resection of the prostate, radical prostatectomy, external beam irradiation of prostate tissue, and other urological interventions which disturb the urethra. Non-limiting examples of diseases or disorders known to be associated with urethral stricture include benign prostatic hypertrophy (BPH), prostate cancer, sexually transmitted diseases and urethral cancer. Further details of tissues which comprise the urethra or which are located in close proximity thereto in the human are found in, for example, Williams et al., eds. (1980, Gray's Anatomy, 36th ed., W.B. Saunders Co., Philadelphia, pp. 1408-1409).

Known treatments for urethral strictures include surgical modification of the urethra, laser-assisted modification of the urethra, urethroplasty, and urethral stent implantation (Bosnjakovic et al., 1994, Cardiovasc. Intervent. Radiol. 17:280-284; Badlani et al., 1995, Urology 45:846-856; Mundy, 1989, Brit. J. Urology 64:626-628; Quartey, 1993, Ann. Urol. 27:228-232).

Ureteric stricture is another known complication of urological procedures and of disease and disorder states. Ureteric strictures may involve hyperplasia or hypertrophy of any of the tissue layers of a ureter, namely the fibrous layer, the muscular layer, or the mucous layer, or may involve hyperplasia or hypertrophy of a tissue or organ located in close proximity to a ureter. Further details of tissues which comprise a ureter or which are located in close proximity thereto in the human are found in, for example, Williams et al., eds. (1980, Gray's Anatomy, 36th ed., W.B. Saunders Co., Philadelphia, pp. 1402-1404). Surgical treatments are known for treatment of ureteric stricture.

Disclosed herein are graduated catheters and methods which may be used to facilitate the localization of a urethral stricture by directly viewing the endo-urethral wound left after a urethrotomy. Once the position of the urethral stricture is located, by directly viewing the lumen of the urethra, and identified, by noting the graduated marking on the catheter corresponding to the urethral stricture, the urethral stricture may be treated. Treatment may include the insertion of a second device having a radiation source to deliver treatment to the urethral stricture. In some implementations, a determination may be made as to the exact distance a radiation source must be inserted into the catheter to reach the urethral stricture before the second device is inserted. In this situation, the distances and/or measurements associated with the location of the urethral stricture may then be converted into offsets (the total distance that the source needs to be extended) and this data may be used in combination with dwell times to formulate a treatment plan. These graduated catheters and methods for use may translate the endoscopic frame of reference into a catheter based frame of reference.

These catheters and methods provide a precise method for identifying the exact location where a therapy device needs to deliver its treatment. If the exact location is not known, or is miscalculated, the treatment may inadvertently be applied healthy tissues (i.e., damaging the healthy tissues), while the target area requiring treatment receives none. If this situation occurs, the damage to surrounding healthy tissues may be detrimental, especially where the treatment comprises radiation dosing using a radiation source. The effects of miscalculating an exact location for treatment planning are both dangerous to the patient's health and expensive (i.e., requiring additional treatments because the initial treatment was delivered inaccurately). Thus, devices and methods for identifying the precise location for treatment delivery would be advantageous for protecting patients and for reducing medical costs.

With reference now to FIG. 1, an elongated graduated catheter 100 is shown positioned within a urethra 150 and anchored against a wall of a bladder 152. The elongated catheter body 100 may be comprised of hollow approximately cylindrical tube comprised of a biocompatible flexible material (silicone, polypropylene, polyurethane, latex, other polymers, etc.) which may be either completely or partially transparent. In one embodiment, the entire catheter 100 body may be transparent. In another embodiment, catheter 100 may have a combination of transparent 120 and non-transparent 122 portions. The elongated catheter 100 has proximal 102 and distal 104 ends. The proximal end 102 may be open or partially open, allowing access to the main lumen 110 and/or secondary lumens, and may also be configured with a handle and/or ports (not shown) for access by a user.

The elongated catheter 100 may also have an anchor 106 disposed on the distal end 104 configured to establish a secure relationship between the elongated catheter 100 and an anatomical feature, such as the bladder 152. In one embodiment, the anchor 106 may comprise an expandable chamber 106, such as a balloon 106. Anchor 106 may be coupled to a secondary lumen (described in more detail below) providing a pathway for inflation/deflation of the balloon 106 operable via the proximal end 102 of the catheter 100. The anchor 106 on the distal end 104 of the catheter 100 may be deflated or compacted for easy insertion into a body lumen and may then be inflated or expanded (shown in FIG. 1) once in position to securely anchor the catheter 100 in place. In this implementation, the anchor 106 may again be deflated or compacted for removal of the catheter 100 through the body lumen upon completion of the procedure.

In another embodiment, the anchor 106 may comprise arms or spikes (not shown) which may be expanded and retracted to anchor the catheter 100 securely in place. In this implementation, the arms or anchors may be in a contracted/retracted position to minimize the catheter profile for insertion into a lumen, and once inserted and positioned, the arms or anchors may be opened or expanded to engage or anchor the catheter with regard to an anatomical feature.

Urethral catheters having anchoring mechanisms are disclosed and further described in U.S. Pat. No. 6,607,477, entitled Graduated Intraluminal Catheter and Methods of Use Thereof, and in copending application Ser. No. 11/152,824, filed on Jun. 14, 2005, and entitled Urethral Radiation Treatment System and Method, both of which are incorporated herein by reference for all that they disclose.

With continuing reference to FIG. 1, the elongated catheter 100 may also have fiducial or graduated markings 108 disposed along a length of the catheter. The graduated markings 108 are visible marks or labels, such as numbers, letters, symbols, or colors, which may be printed, etched, or embedded along the length of the catheter. The graduated markings 108 are disposed such that they can be visualized from within the catheter main lumen, so that a user can note the specific graduated marking 108 corresponding to a specific anatomical feature within the body lumen, such as the precise location (i.e., graduated marking) of a urethral stricture with a urethra, for example. The graduated markings 108 may be used by a urologist, radiologist, or other user to identify a precise location or depth of a specific anatomical feature within a body lumen. Said another way, the graduated markings 108 provide a landmark or frame of reference to specifically identify the position of an anatomical feature in relation to the graduated marking 108.

Figure 2:
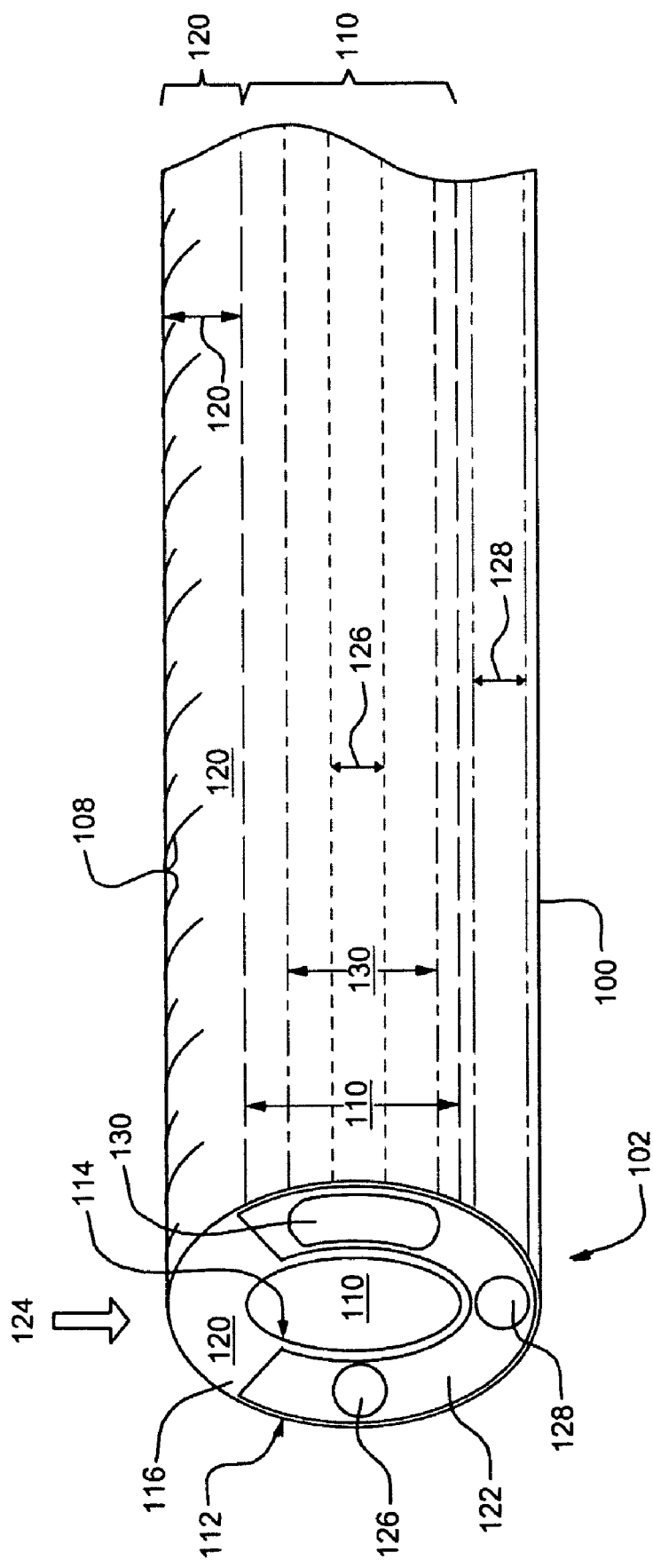
FIG. 2 illustrates a cross-sectional view in elevation of an exemplary graduated catheter.

With reference now to FIG. 2, the catheter 100 has outer 112 and inner 114 surfaces defining a catheter wall 116. Catheter wall 116 may have any number of different shapes and have any thickness, but in some implementations, may be thick enough to include secondary lumens disposed therein. The outer surface 112 of the catheter wall 116 is configured for contacting a body lumen. The inner surface 114 of the catheter wall 116 defines a main lumen 110 disposed along a length of the elongated catheter 100. The main lumen 110 may be approximately circular, oblong, or a regularly shaped polygon, such as a hexadecagon (i.e., a 16-sided polygon), for example. The main lumen 110 is sized for receiving a visualization tool therein. The catheter wall 116 is transparent along a length to provide visualization of the graduated markings 108 via a visualization tool, such as a cytoscope, endoscope, hysteroscope, or other fiberoptic system, positioned in the main lumen 110.

The catheter 100 may further comprise a mechanism (not shown) to irrigate the outer surface 114 of the catheter 100 in order to clear the field of view of fluids, such as blood or urine, often associated with such surgical procedures. A mechanism for irrigating the outer surface 114 of the catheter 100 may comprise one or more ports coupled to fluid irrigation and/or suction lumens to help maintain a clear field of view during the procedures.

Catheter 100 has a substantially circular cross-section, as shown in FIG. 2, and may be formed of a combination of transparent material 120 (either optically clear or translucent) and non-transparent material 122 (either opaque or pigmented). The transparent portion 120 of the catheter 100 may be formed of any appropriate optically clear biocompatible material to help achieve proper placement of the catheter in vivo. The non-transparent portion 122 of the catheter may be formed of any appropriate non-transparent biocompatible material and may be black.

The transparent portion 120 may be formed to be angular from the centerline of the catheter 100. In this embodiment, the catheter wall 116 may comprise an arc-shaped transparent window as viewed from the cross-section of the central or main lumen 110 of catheter 100. Said another way, when viewing the cross-section of the substantially circular catheter 100, the arc-shaped transparent window may look similar to that of a slice of pie. Of course, it is anticipated that various different sizes and shapes of the transparent portion 120 of the catheter 100 may be utilized herein. For example, in some implementations the transparent portion 120 may not be angular from the center of the catheter 100 (i.e., may not be slice of pie-shaped) and may be formed in any number of specific sizes.

In one example shown in FIG. 2, the transparent portion 120 may comprise an approximately 60° arc-shaped transparent window, shown as 120, with the remaining approximately 300° section of the catheter wall 116 being non-transparent portion 122. In another example, the transparent portion 120 may comprise an approximately 90° arc-shaped transparent window 120, with the remaining approximately 270° section of the catheter wall 116 being non-transparent portion 122. Transparent portion 120 may also be formed to be smaller than or less than an approximately 60° arc-shaped transparent window or to be larger than an approximately 90° arc-shaped transparent window and may be formed in any unlimited number of specific sizes. The specific size examples given herein are exemplary only for purposes of illustration.

With continued reference to the cross-sectional view of an approximately circular catheter 100, it is further anticipated that more than one transparent portion 120 may be utilized in combination with more than one non-transparent portion 122. For example, a catheter may comprise two or more separate and spaced apart transparent window portions 120. In this implementation, the separate and spaced apart transparent window portions 120 may be separated by more than one separate and spaced apart non-transparent portions 122.

In yet another embodiment, catheter may be formed entirely of transparent materials, proving a full 360° field of view. In this implementation, a user would have unlimited viewing capabilities via a visualization tool. In an alternative implementation, the entirely transparent catheter may be used in combination with a special purpose endoscope or cytoscope, which would optimize image quality by providing an angled imaging geometry, such as a 90° field of view, for example. Alternatively, a user may use a substantially transparent catheter in combination with any existing remote visualization tools.

The non-transparent portion 122 of a catheter 100 may be advantageous for several reasons, such as ensuring that a user utilizes only a predetermined transparent portion 120 of the catheter 100 for viewing by shielding the user's view from other non-pertinent anatomy of the body lumen. The non-transparent portion 122 may also ensure a specific rotational orientation of the catheter once implanted. For example, because urethrotomy wounds are typically found at the 12-o'clock position within the urethra, the catheter 100 may be inserted with the transparent portion 122 in the 12-o'clock position (shown by arrow 124) to provide an unobstructed view of the urethra at 12-o'clock position.

The non-transparent, opaque, or pigmented portion 122 of the catheter 100 also serves to enhance visualization through the transparent portion 120 of the catheter 100 by reducing the amount of light that is reflected (i.e., reflective glare) by the non-transparent portion 122 of the catheter 100. The non-transparent portion 122 may also reduce parallax effects by providing an angled imaging geometry.

The non-transparent, opaque, or pigmented portion 122 of the catheter 100 may also be formed of a radiation attenuating or shielding material to reduce or block radiation through the non-transparent portions of the catheter 100. In this embodiment, the non-transparent portion 122 may be formed in a predetermined size or shape to provide radiation attenuation or shielding in a predetermined shape to tissues adjacent the catheter 100.

The catheter 100 may also include one or more secondary lumens 126, 128, 130 for performing additional or supplementary medical procedures. As shown in FIG. 2, the secondary lumens 126, 128, 130 may be disposed within the opaque or non-transparent portion 122 of catheter 100. The secondary lumens 126, 128, 130 may be circular (126, 128) or irregular shaped (130) to accommodate the insertion of medical instruments or other devices.

The secondary lumens 126, 128, 130 may provide pathways for drainage of fluids, and/or for inflation or deployment of the anchor 106, and/or for insertion of a stiffening element (described in more detail below), and/or for insertion of a radiation source(s) or other source of therapeutic rays or treatment. It is anticipated that catheter 100 may have one, two, or more lumens located in either the transparent or clear region 120, or in the opaque or non-transparent region 122, or may have lumens in both regions.

Catheter 100 may further comprise a stiffening element, such as a metallic cable, wire or rod, to provide the catheter 100 with some rigidity. In some implementations this stiffening element may be bent or manipulated to retain a shape to better match the unique anatomical features of a body lumen of a patient. In one embodiment, the stiffening element may comprise a cable threaded through one of the secondary lumens 126, 128, 130. In another embodiment, the stiffening element may comprise a high durometer elastomeric material which provides increased stiffness along the catheter length for ease of placement and/or for reduction of friction.

Figure 3A:
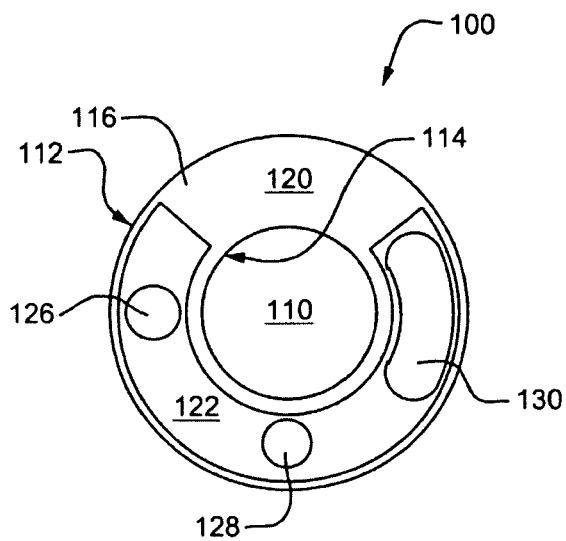
FIG. 3A illustrates a cross-sectional end view of a first embodiment of an exemplary catheter.

FIG. 3A illustrates an end view of a first exemplary catheter 100 in cross-section. The catheter 100 is comprised of an opaque segment 122 embedded in the optically clear wall 116 of the catheter. The catheter 100 contains a large main lumen 110, disposed approximately centrally, which serves as a pathway for both the visualization tool, such as a cytoscope, endoscope, hysteroscope, or other fiberoptic system, and later a treatment catheter.

FIG. 3A also illustrates three secondary lumens disposed within the non-transparent portion 122. Catheter 100 includes a large irregularly shaped secondary lumen 130 which may be used for drainage of urine, a smaller secondary lumen 126 which may be used for inflation of an anchoring balloon 106, and another smaller secondary lumen 128 in which may be embedded a non-elastic material (e.g. a metallic cable) for rigidity or stiffening of the catheter 100. Of course, the specific purposes of the secondary lumens 126, 128, 130 may vary with procedures and specific applications and the examples give above are exemplary only for purposes of illustration herein.

Figure 3B:
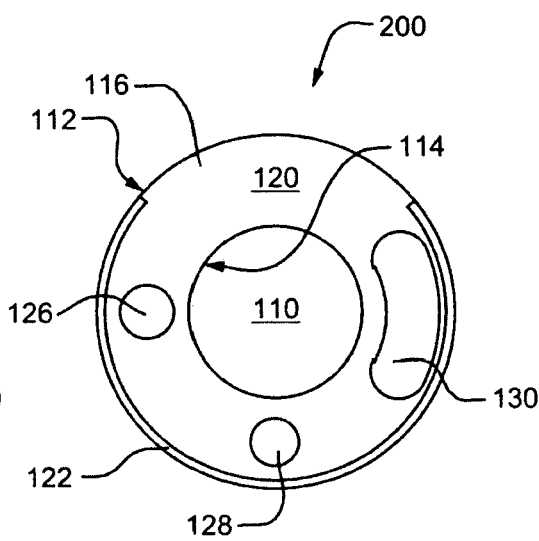
FIG. 3B illustrates a cross-sectional end view of a second embodiment of an exemplary catheter.

FIG. 3B illustrates a second embodiment of an exemplary catheter 200 in cross-section. The catheter 200 has outer 112 and inner 114 surfaces defining a catheter wall 116. Inner surface 114 of catheter wall 116 defines a substantially central main lumen 110. In this implementation, the body of catheter 200 is substantially comprised of a transparent portion 120, which may also contain at least one secondary lumen(s) 126, 128, 130. Catheter 200 also includes a non-transparent portion 122 which may comprise an open ring-shaped segment disposed along or attached to the outer surface 112 or outer perimeter of the catheter 200. As described above, the non-transparent portion 122 of catheter 200 contains pigments that reduce the amount of light reflected by the non-transparent portion 122 of the catheter 200. In one implementation, the non-transparent portion 122 may also be adjustable and/or removable to provide varying fields of view and/or to provide an entirely transparent 120 catheter when desired.

Figure 3C:
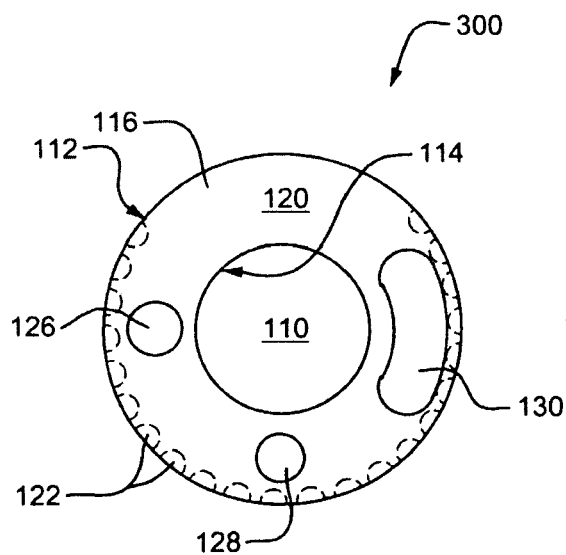
FIG. 3C illustrates a cross-sectional end view of a third embodiment of an exemplary catheter.

FIG. 3C illustrates a third embodiment of an exemplary catheter 300 in cross-section. The catheter 300 has outer 112 and inner 114 surfaces defining a catheter wall 116. Inner surface 114 of catheter wall 116 defines a substantially central main lumen 110. In this implementation, the body of catheter 300 is substantially comprised of a transparent portion 120, which may also contain at least one secondary lumen(s) 126, 128, 130. Catheter 300 also includes a non-transparent portion 122 consisting of separate smaller opaque segments 122. As described above, the non-transparent portion 122 of catheter 300 contains pigments that reduce the amount of light reflected by the non-transparent portion 122 of the catheter 300. FIG. 3C illustrates the arrangement of the opaque segments 122 either on or embedded in the outer surface 112 of the catheter wall 116, in which the opaque segments 122 consist of a series of separate segments co-extruded into the transparent portion 120 of the catheter wall 116.

Figure 4:
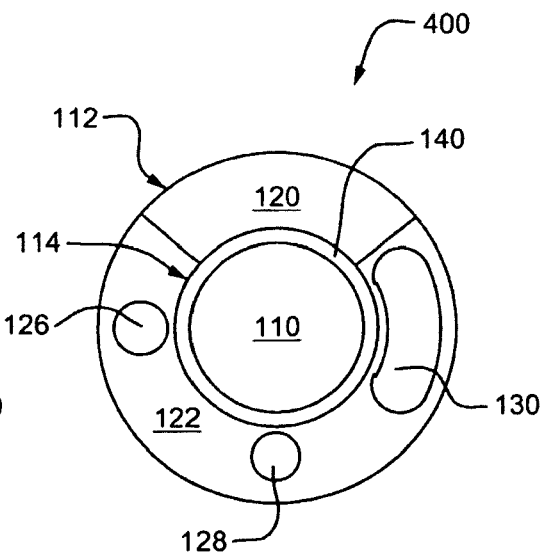
FIG. 4 illustrates a cross-sectional end view of an exemplary catheter having a stiffening element.

FIG. 4 illustrates a fourth embodiment of an exemplary catheter 400 in cross-section. The catheter 400 has outer 112 and inner 114 surfaces defining a catheter wall 116. Inner surface 114 of catheter wall 116 defines an approximately circular stiffening element 140, which defines a substantially central main lumen 110. The stiffening element 140 defining the main lumen 110 may be formed of a high hardness (i.e., durometer) material to provide increased stiffness along the length for ease of placement and/or for reduction of friction. The higher stiffness material 140 may provide additional stretch resistance or lower surface friction to facilitate easier placement of the visualization tool and the treatment catheter. In this implementation, the body of catheter 400 is substantially comprised of a non-transparent portion 122, which may also contain at least one secondary lumen(s) 126, 128, 130. Catheter 400 also includes a transparent portion 120 consisting of an arc-shaped window portion.

Figure 5:
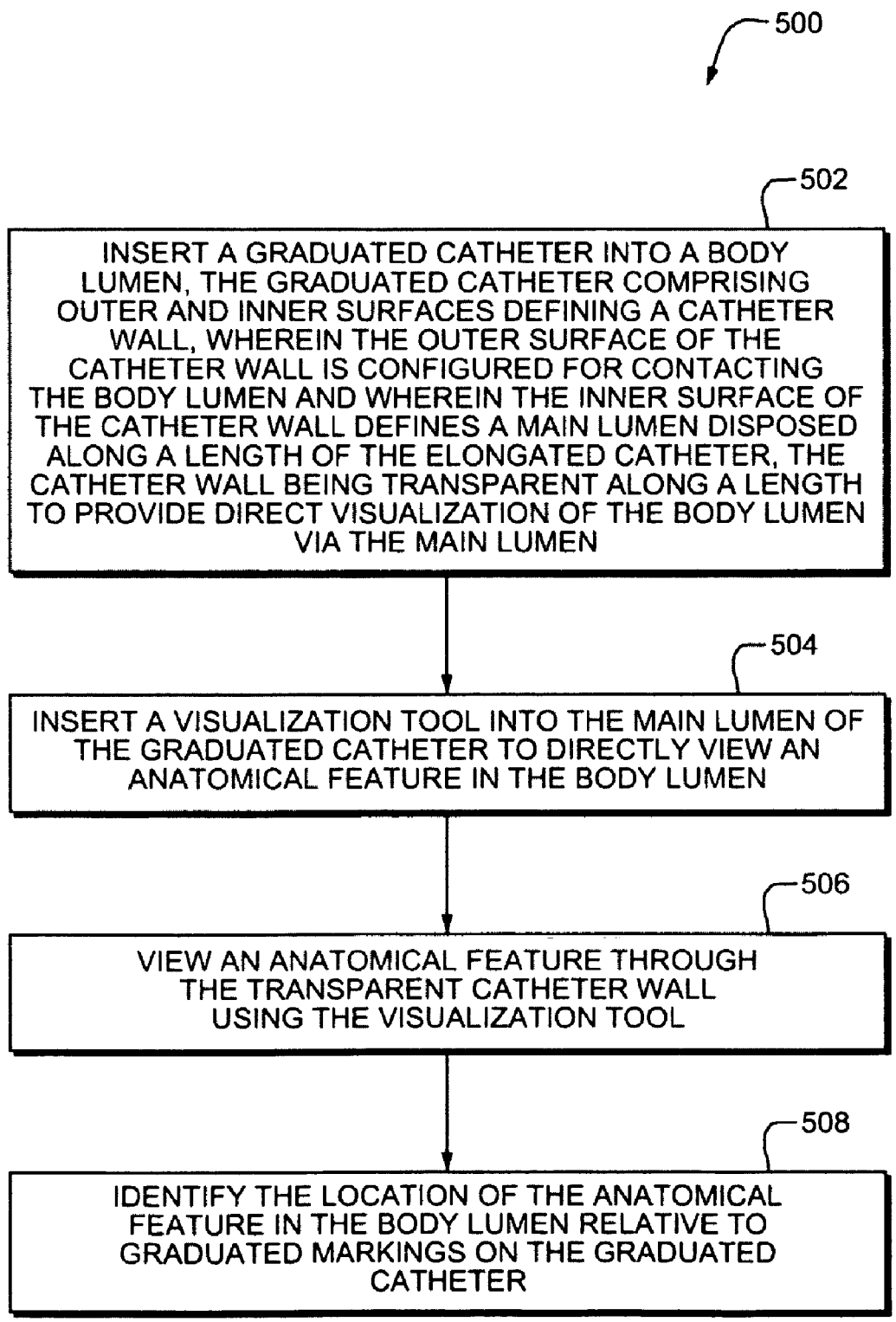
FIG. 5 is a flow diagram illustrating an exemplary method for directly identifying an anatomical feature in a body lumen.

The method 500 of identifying an anatomical feature in a body lumen comprises the insertion 502 of a graduated catheter into a body lumen, as illustrated in a flow chart at FIG. 5 and shown in vivo in FIG. 1. For patient-comfort, the outer surface 112 of the graduated catheter 100 may be coated with an anesthetics and/or lubricants to ease insertion of the device into a body lumen of a patient. The elongated catheter 100 may be inserted through the urethra 150 and into the bladder 152 with the anchor balloon 106 in the deflated or compacted position (not shown) to minimize the insertion profile of the catheter 100. At this point it may also be necessary to drain the patient's bladder 152.

Once the anchor balloon 106 on the distal end 106 of the catheter 100 is positioned within the bladder 152 (or other desired anatomical feature), it may be fully inflated and then gently pulled (as if to remove the catheter 100 from patient) to securely seat the anchor balloon 106 against the bladder 152 wall at entrance to the urethra 150. The anchor balloon 106 provides a mechanism for securely anchoring the catheter 100 in place and prevents the catheter 100 from moving or slipping out during a treatment procedure. Once the prescribed therapeutic treatment has been delivered the anchor balloon 106 may be deflated to compact the anchor balloon 106 for easier removal from the body lumen.

Once the catheter 100 has been inserted 502 and anchored in place, a remote visualization tool may be inserted 504 through the main lumen 110 of the catheter 100 and advanced until the user, typically a urologist or radiologist, can visualize or view 506 an anatomical feature, such as a urethral stricture, through the transparent portion 120 of the catheter 100. A lubricant may be used to ease insertion of the visualization tool through the main lumen 110 of the catheter 100. A camera or other display coupled to the visualization tool will provide a urologist or radiologist with a view of the body lumen and the anatomical feature as seen through the transparent portion 120 of the catheter 100. Once the anatomical feature has been viewed 506, it is then possible to specifically identify 508 the location of the anatomical feature in the body lumen relative to the graduated markings 108 on the catheter 100 by reading the graduated markings 108 corresponding to the anatomical feature. By viewing the graduated markings 108 a determination can be made as to the precise location of the anatomical feature, such as a urethral stricture, in the patient.

Typically, a practitioner will determined the proximal and distal ends of a urethral stricture and then pass that information on to a radiation oncologist who then determines the distance a treatment source must be inserted into the catheter 100 to reach the urethral stricture. In practice, the treatment sources must be placed such that the target lesion plus a margin distal and proximal to the lesion receives a prescribed dose of therapeutic treatment. Treatment sources include, but are not limited to radionuclides, x-rays, ultrasound, radiofrequency (RF), hyperthermia, and laser.

In one exemplary urethral application, a method may comprise: i) inserting a graduated catheter into a patient's urethra; ii) advancing the graduated catheter until the deflated balloon anchor on the distal end of the catheter is within the patient's bladder; iii) inflating the anchor balloon on the distal end of the graduated catheter to deploy the balloon anchor; iv) gently pulling on the graduated catheter to securely seat the balloon anchor against the bladder wall at the entrance to the urethra; v) inserting a visualization tool into the main lumen of the graduated catheter to directly view an anatomical feature in the body lumen; vi) viewing the anatomical feature through the transparent catheter wall using the visualization tool; vii) identifying the depth location of the anatomical feature in the body lumen relative to graduated markings on the graduated catheter; viii) removing the visualization tool and inserting a radiation source to the depth location identified to delivery brachytherapy treatment to the anatomical feature at the identified location.

It is also anticipated that the devices and methods disclosed herein will have utility outside the field of urethral brachytherapy. For instance, it may be desirable to treat other tissues with therapeutic rays. One example is the treatment of the prostate. The prostate is a solid organ which surrounds the urethra of the male human between the base of the bladder and the urogenital diaphragm. Benign prostatic hypertrophy (BPH) is a common condition among male humans aged 45 or older. Prostate cancer is a leading cause of death among males, and can frequently be diagnosed with the aid of a simple blood antigen-detecting test. Radiation therapy and prostatectomy are the primary treatments available for prostate cancer and prostatectomy is currently the primary treatment for BPH. Prostatectomy has numerous drawbacks, which have been widely described in the art. External beam irradiation of the prostate for the treatment of localized prostate cancer is associated with small bowel injury, radiation proctitis, and urethral stricture (Gibbons et al., 1979, J. Urol. 121:310-312). At least two groups have employed transurethral radiation therapy as a supplement to external beam irradiation of localized prostate cancer tissue (Harada et al., 1993, Rad. Oncol. 11:139-145; Skarlatos et al., 1994, Urol. Int. 53:209-213). In addition, another group has employed transurethral radiation therapy as a sole treatment for recalcitrant BPH-related urine retention (Koukourakis et al., 1994, Med. Dosimetry 19:67-72). Each of these groups employed ultrasonography, computerized tomography, or fluoroscopy imaging methods to identify the tissue to be treated or to confirm the position of the radiation source relative to the tissue to be treated. Identification of the location of tissue in need of treatment and placement of a radiation source using one of these imaging methods is dependent upon the deformability of the tissues being imaged, the body posture of the subject during the identification or placement, the position of the imaging device, and other factors which may not be easily replicated.

Failure to precisely control the amount and location of transurethrally-delivered radiation can result in damage to the urethra itself or to other organs located in close proximity thereto, including the bladder, rectum and prostate. It is thus critical to identify the position of a tissue in need of treatment and the location of radiation source as accurately as possible.

A person of ordinary skill in the art will appreciate further features and advantages of the devices and methods disclosed herein based on the above-described embodiments. For example, specific features from any of the embodiments described above as well as in U.S. Pat. No. 6,607,477 and in copending application Ser. No. 11/152,824, filed on Jun. 14, 2005, may be incorporated into devices, systems, and/or methods disclosed herein in a variety of combinations and subcombinations, as well as features referred to in the claims below which may be implemented by means described herein. In particular, the graduation and visualization means may be used in any number of combinations, as well as the sources of therapeutic rays, from any of these sources.

Accordingly, the devices and methods disclosed herein are not to be limited by what has been particularly shown and described, except as indicated by the appended claims or those ultimately provided. Any publications and references cited herein are expressly incorporated herein by reference in their entirety.

What is claimed is:

1. An elongated catheter, comprising: proximal and distal ends; the elongated catheter having a substantially circular cross-section;
   an anchor disposed on the distal end of the elongated catheter configured to establish a secure relationship between the elongated catheter and an anatomical feature;
   graduated markings disposed along a length of the catheter; and
   outer and inner surfaces defining a catheter wall, wherein the outer surface of the catheter wall is configured for contacting a body lumen and wherein the inner surface of the catheter wall defines a main lumen disposed along a length of the elongated catheter, the catheter wall having an approximately 60° arc-shaped transparent window along a length of the elongated catheter to provide visualization of the graduated markings via a visualization tool positioned in the main lumen, wherein a remaining 300° arc-shaped section of the catheter wall is substantially opaque and formed of a radiation attenuating material to reduce or block radiation from a radiation source disposed within the catheter.

2. The elongated catheter of claim 1, wherein the catheter wall further comprises at least one secondary lumen disposed in the catheter wall and operably coupling the proximal and distal ends of the catheter.

3. The elongated catheter of claim 2, wherein the at least one secondary lumen provides an inflation pathway to deploy the anchor.

4. The elongated catheter of claim 2, wherein the at least one secondary lumen provides a drainage pathway to remove fluid from a body lumen.

5. The elongated catheter of claim 1, wherein the proximal end further comprises an opening for accessing the main lumen, the opening sized for receiving a visualization tool.

6. The elongated catheter of claim 1, wherein the anchor comprises an inflatable chamber.

7. The elongated catheter of claim 1, further comprising a stiffening element, wherein the stiffening element is threaded through a secondary lumen in the catheter wall.

8. The elongated catheter of claim 1, wherein the elongated catheter has a substantially circular cross-section and wherein the substantially circular catheter wall is substantially transparent.

9. The elongated catheter of claim 1, further comprising a source of therapeutic rays disposed within the main lumen of the elongated catheter.

10. The elongated catheter of claim 1, wherein the visualization tool comprises a surgical scope having an illumination source configured to illuminate and visualize the interior of the body lumen.

11. The elongated catheter of claim 1, wherein the graduated markings comprise at least one of: numbers, letters, symbols, or color-coding.

12. The elongated catheter of claim 1 wherein the remaining 300° arc-shaped section includes pigments that reduce reflectivity.

13. A graduated catheter, comprising:
outer and inner surfaces defining a catheter wall, wherein the outer surface of the catheter wall is configured for contacting a body lumen and wherein the inner surface of the catheter wall defines a main lumen disposed along a length of the graduated catheter;
wherein the catheter wall has a substantially circular cross-section including an approximately 60° arc-shaped transparent window for viewing graduated markings on the catheter relative to the body lumen via a visualization tool positioned in the main lumen and wherein a remaining portion of the substantially circular cross-section of the catheter wall is non-transparent and formed of a radiation attenuating material to reduce or block radiation from a radiation source disposed within the catheter.

14. A method for directly identifying an anatomical feature in a body lumen, the method comprising:
inserting a graduated catheter into a body lumens the graduated catheter comprising outer and inner surfaces defining a catheter wall, wherein the outer surface of the catheter wall is configured for contacting the body lumen and wherein the inner surface of the catheter wall defines a main lumen disposed along a length of the elongated catheter, wherein the elongated catheter has a substantially circular cross-section, and wherein the catheter wall has an approximately 60° arc-shaped transparent window along a length to provide direct visualization of the body lumen via the main lumen and wherein a remaining portion of the substantially circular cross-section of the catheter wall is non-transparent and formed of a radiation attenuating material to reduce or block radiation from a radiation source disposed within the catheter;
inserting a visualization tool into the main lumen of the graduated catheter to directly view an anatomical feature in the body lumen;
viewing the anatomical feature through the transparent catheter wall using the visualization tool; and
identifying the location of the anatomical feature in the body lumen relative to graduated markings on the graduated catheter.

15. The method of claim 14, further comprising converting the location of the anatomical feature into a measurement applicable for insertion of a radiation source for brachytherapy treatment.

16. The method of claim 14, further comprising treating the anatomical feature in the body lumen by inserting a radiation source via the main lumen to deliver a therapeutic dose of radiation.

17. The method of claim 14, further comprising irrigating the outer surface of the catheter to clear fluids to enhance visibility of the body lumen and graduated markings using the visualization tool.

18. The method of claim 14, further comprising deploying an anchor coupled to a distal end of the graduated catheter to seat the graduated catheter securely against an anatomical feature.

19. The method of claim 14, wherein the anatomical feature is a urethral stricture.

20. The method of claim 14, wherein the visualization tool is an endoscope.

21. The method of claim 14, further comprising illuminating the main lumen to enhance visualization of the anatomical feature in the body lumen and the graduated markings.

22. The method of claim 14, wherein inserting further comprises inserting in a predetermined orientation to optimize rotational orientation of the catheter in the body lumen.

23. An elongated catheter, comprising: proximal and distal ends; the elongated catheter having a substantially circular cross-section;
an anchor disposed on the distal end of the elongated catheter configured to establish a secure relationship between the elongated catheter and an anatomical feature;
graduated markings disposed along a length of the catheter; and
outer and inner surfaces defining a catheter wall, wherein the outer surface of the catheter wall is configured for contacting a body lumen and wherein the inner surface of the catheter wall defines a main lumen disposed along a length of the elongated catheter, the catheter wall comprising two or more separate and spaced apart transparent portions and a non-transparent portion, at least a part of the non-transparent portion being formed of a radiation attenuating material to reduce or block radiation from a radiation source disposed within the catheter.

24. The elongated catheter of claim 23, wherein the non-transparent portion comprises two or more separate and spaced apart non-transparent portions such that the two or more separate and spaced apart transparent portions are separated by at least one of the two or more separate and spaced apart non-transparent portions.

* * * * *